United States Patent [19]
Nick et al.

[11] Patent Number: 6,096,900
[45] Date of Patent: Aug. 1, 2000

[54] SOLVENTLESS PREPARATION OF PHTHALIMIDES

[75] Inventors: Robert Joseph Nick, Dunstable, Mass.; Mark Erik Nelson, Mount Vernon, Ind.; Joseph John Caringi, Niskayuna; Drew Elliot Williams, Scotia, both of N.Y.

[73] Assignee: General Electric Company, Schenectady, N.Y.

[21] Appl. No.: 09/418,871

[22] Filed: Oct. 15, 1999

Related U.S. Application Data

[62] Division of application No. 09/307,021, May 7, 1999.
[51] Int. Cl.$^7$ .................................................. C07D 209/48
[52] U.S. Cl. ............................................... 548/462
[58] Field of Search ............................................. 548/462

[56] References Cited

U.S. PATENT DOCUMENTS

| | | | |
|---|---|---|---|
| 4,536,582 | 8/1985 | Markle | 548/477 |
| 4,644,066 | 2/1987 | Sonnenberg | 548/462 |
| 5,233,049 | 8/1993 | Dinan et al. | 548/462 |
| 5,470,987 | 11/1995 | Inbasekaran | 548/462 |
| 5,977,289 | 11/1999 | Yang et al. | 527/185 |

OTHER PUBLICATIONS

J.C. Sheehan and V.S. Frank, *J. Am. Chem. Soc.*, vol. 71, pp. 1856–1861 (1949).

*Organic Syntheses*, Collective vol. 3, pp. 151–156 (1955).

P.M. Hergenrother and S.J. Havens, *Journal of Polymer Science: Part A: Polymer Chemistry*, vol. 27, pp. 1161–1174 (1989).

*Primary Examiner*—Deborah C. Lambkin
*Attorney, Agent, or Firm*—Bruce S. Brown; Noreen C. Johnson

[57] ABSTRACT

A method for the solventless synthesis of a phthalimide or phthalimide mixture is provided comprising contacting at least one amine reactant and at least one anhydride reactant in a solventless environment at a first temperature sufficient to allow the reactants to at least partially condense; and increasing the temperature to a second temperature sufficient to melt the reaction mixture, thereby allowing the reaction to go essentially to completion and form the reaction product.

30 Claims, No Drawings

SOLVENTLESS PREPARATION OF PHTHALIMIDES

This application is a division of Ser. No. 09/307,021 May 7, 1999, allowed.

BACKGROUND OF THE INVENTION

The present invention relates to a method for preparing phthalimides. In particular, this invention relates to an environmentally friendly, solventless method for the preparation of tris(phthalimide)s, bis(phthalimide)s, mono (phthalimide)s, and mixtures thereof.

Tris(phthalimide)s, bis(phthalimide)s and mono (phthalimide)s are useful branching monomers, polymerizable monomers and end-capping monomers, respectively, for polymer synthesis. For example, chlorophthalimides are useful as intermediates in the synthesis of condensation polymers. The bis(chlorophthalimide) having the formula (I) is a polymerizable monomer useful in the synthesis of polyetherimides:

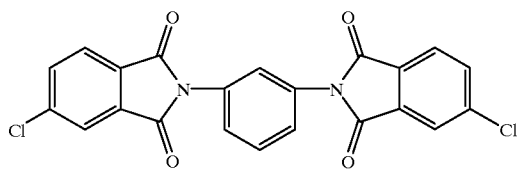

The phthalimide of formula (I) is typically prepared by catalysis under conditions of total reflux in glacial acetic acid or in other organic solvents from which the water of reaction is removed by azeotropic distillation. Typically, the solid monomer is only soluble up to about 2% by weight, and thus cannot be readily used in situ, but must be isolated by filtration, washing and drying.

Many different phthalimides are typically made using solvent-based processes. The use of solvents presents environmental and cost concerns. One commonly used organic solvent in such processes is o-dichlorobenzene, which is not environmentally benign. Other, more environmentally benign solvents have been examined, but have been found to provide in general slower reaction, less conversion to product, and more impurities than are desirable in a manufacturing situation.

Accordingly, there remains a need for improved, environmentally sound, economical methods for producing phthalimides such as mono-, bis-, and tris(chlorophthalimide)s. Such methods must also have good reaction rates and high percent conversion to a product isolable in a convenient, usable physical form.

SUMMARY OF THE INVENTION

In one embodiment the method of the present invention comprises solventless synthesis of a phthalimide or phthalimide mixture of formula (II)

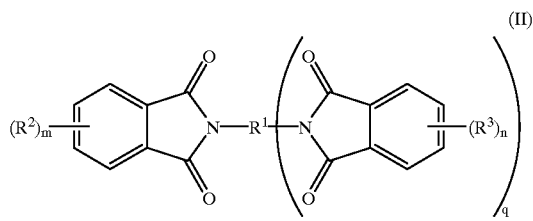

wherein $R^1$ is a mono-, di-, or trivalent organic radical, and $R^2$ and $R^3$ are each independently halogen, nitro, nitroso, alkyl, aryl, or mixtures thereof; m and n each independently have values between 0 and 4 inclusive; and q is 0, 1, or 2.

In another embodiment the method comprises heating a mixture of at least one amine reactant and at least one anhydride reactant in a solventless environment to a first temperature sufficient to allow the reactants to at least partially condense; and increasing the temperature to a second temperature sufficient to melt the reaction mixture, thereby allowing the reaction to go essentially to completion and form phthalimide product.

In yet another embodiment the method comprises heating a mixture of at least one amine reactant and at least one anhydride reactant in a solventless environment to a first temperature sufficient to allow the reactants to at least partially condense; cooling the reaction mixture; and heating the reaction mixture to a second temperature at which it remains substantially solid under reduced pressure, thereby essentially completing formation of a phthalimide or phthalimide mixture.

In still another embodiment the method comprises heating an amic acid or amic acid mixture (derived from reaction of at least one amine reactant and at least one anhydride reactant) to a temperature at which it remains substantially solid in a solventless environment under reduced pressure, thereby essentially completing formation of a phthalimide or phthalimide mixture.

DETAILED DESCRIPTION OF THE INVENTION

The present invention provides methods for the synthesis of phthalimides of formula (II), wherein at least one amine reactant is reacted with at least one anhydride reactant in a solventless environment. Amines suitable for use in the methods include those of formula (III)

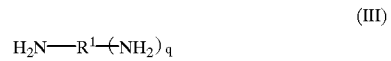

wherein $R^1$ is a mono-, di-, or trivalent organic radical, and q is 0, 1, or 2. $R^1$ may be any organic group that does not interfere with the reaction. For example, the $R^1$ group should not be so large that it inhibits the desired reaction because of steric hindrance. Preferably, $R^1$ is selected from the group consisting of aliphatic, aromatic, and heterocyclic moieties.

Exemplary aliphatic moieties include, but are not limited to, straight-chain-, branched-, and cycloalkyl radicals, and their substituted derivatives. Straight-chain and branched alkyl radicals are preferably those containing from 1 to 26 carbon atoms, and include as illustrative non-limiting examples ethyl, propyl, butyl, neopentyl, hexyl, dodecyl. Cycloalkyl radicals are preferably those containing from 3 to 12 ring carbon atoms. Some illustrative non-limiting examples of cycloalkyl radicals include cyclobutyl, cyclopentyl, cyclohexyl, methylcyclohexyl, and cycloheptyl.

The two or three amino groups in diamine and triamine aliphatic moieties are preferably each separated from another amino group by at least two and most preferably by at least three carbon atoms. In especially preferred embodiments for diamines, the two amino groups are in the alpha, omega positions of a straight-chain or branched alkyl radical, or their substituted derivatives; or in the 1,4-positions of a cycloalkyl radical or its substituted derivatives. In especially preferred embodiments for triamines, two amino groups are in the alpha, omega positions of a straight-chain or branched alkyl radical, or their substituted derivatives; or in the 1,4-positions of a cycloalkyl radical or its substituted derivatives; and the third amino group is separated from any another amino group by at least two and most preferably by at least three carbon atoms.

Preferred substituents for said aliphatic moieties include one or more halogen groups, preferably fluoro, chloro, or bromo, or mixtures thereof; or one or more aryl groups, preferably phenyl groups, alkyl- or halogen-substituted phenyl groups, or mixtures thereof. Most preferably substituents for aliphatic moieties, when present, are chloro or unsubstituted phenyl.

Aromatic moieties suitable for $R^1$ in formula (III) include, but are not limited to, monocyclic, polycyclic and fused aromatic compounds having from 6 to 30, and preferably from 6 to 18 ring carbon atoms, and their substituted derivatives. Polycyclic aromatic moieties may be directly linked (such as, for example, biphenyl) or may be separated by 1 or 2 atoms comprising linking moieties. Representative linking moieties include, but are not limited to, carbonyl, phosphinyl, O, S, $SO_2$, $C_{1-6}$ aliphatic, such as isopropylidene and methylene. Illustrative non-limiting examples of aromatic moieties include phenyl, biphenyl, naphthyl, bis (phenyl)methane, bis(phenyl)-2,2-propane, and their substituted derivatives. Preferred substituents include one or more halogen groups, preferably fluoro, chloro, or bromo, or mixtures thereof; or one or more straight-chain-, branched-, or cycloalkyl groups having from 1 to 26 carbon atoms, preferably methyl, ethyl, propyl, isopropyl, tert-butyl, or mixtures thereof. Most preferably, substituents for aromatic moieties, when present, are at least one of chloro, methyl, ethyl or mixtures thereof.

The two or three amino groups in diamine and triamine aromatic moieties are preferably separated by at least two and most preferably by at least three ring carbon atoms. When the amino group or groups are located in different aromatic rings of a polycyclic aromatic moiety, they are preferably separated from the direct linkage or from the linking moiety between any two aromatic rings by at least two and most preferably by at least three ring carbon atoms. Especially preferred aromatic mono-amines for the embodiments of the present invention include aniline. Especially preferred diamines for the embodiments of the present invention include meta-phenylenediamine; para-phenylenediamine; mixtures of meta- and para-phenylenediamine; isomeric 2-methyl- and 5-methyl-4,6-diethyl-1,3-phenylenediamines or their mixtures; bis(4-diaminophenyl)-2,2-propane; and bis(2-chloro-4-amino-3,5-diethylphenyl)methane.

Heterocyclic moieties suitable for $R^1$ in formula (III) include, but are not limited to, monocyclic, polycyclic and fused heterocyclic compounds having from 3 to 30, preferably from 5 to 13 ring carbon atoms, and 1 to 4 ring heteroatoms. The ring heteroatoms include, but are not limited to, oxygen, nitrogen, sulfur, or combinations thereof. Preferably, ring heteroatoms are nitrogen. Polycyclic heterocyclic moieties may be directly linked (such as, for example, bipyridyl) or may be separated by 1 or 2 atoms comprising linking moieties. Representative linking moieties include, but are not limited to, carbonyl, phosphinyl, O, S, $SO_2$, $C_{1-6}$ aliphatic, such as isopropylidene and methylene.

The two or three amino groups in diamine and triamine heterocyclic moieties are preferably separated by at least two and most preferably by at least three ring atoms. When the amino group or groups are located in different heterocyclic rings of a polycyclic heterocyclic moiety, they are preferably separated from the direct linkage or from the linking moiety between any two heterocyclic rings by at least two and most preferably by at least three ring atoms. Exemplary heterocyclic moieties include, but are not limited to, furyl, pyridyl, bipyridyl, pyrryl, pyrazinyl, pyrimidyl, pyrazolyl, thiazyl, thienyl, bithienyl, and quinolyl.

Anhydrides suitable for use in the present invention have formula (IV)

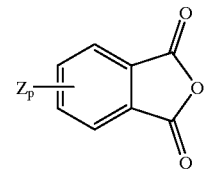

(IV)

wherein Z is a moiety which may be any organic group that does not interfere with the reaction. In one embodiment Z is a displaceable group which participates in a subsequent polymerization reaction. Preferably, Z is halogen, nitro, nitroso, an aliphatic or aromatic moiety as defined above, or mixtures thereof; and p has values between 0 and 4 inclusive. More preferably, Z is halogen, and most preferably chlorine. Especially preferred anhydrides include 3-chlorophthalic anhydride, 4-chlorophthalic anhydride, and dichloro phthalic anhydride. It should be clear that Z groups in formula (IV) correspond to $R^2$ and $R^3$ groups in formula (II).

The reaction between at least one amine reactant and at least one anhydride reactant by the methods of the present invention results in products comprising phthalimides of formula (II). In formula (II) $R^1$ is mono-, di-, or trivalent organic radical as defined for formula (III) above; $R^2$ and $R^3$ are each independently halogen, nitro, nitroso, an aliphatic or aromatic moiety, or mixtures thereof, as defined for Z in formula (IV) above; q is 0, 1, or 2; and m and n each independently have values between 0 and 4 inclusive.

Solventless synthesis is a general reaction, which may be used to produce a variety of phthalimide branching monomers, polymerizable monomers and end-capping monomers, or their mixtures for use, for example, in polymer synthesis. Branching monomer in the present context means a monomer with at least three reactive sites, which is capable of serving as a branching nexus for a polymer chain. Polymerizable monomer in the present context means a monomer with at least two reactive sites capable of participating in a polymerization reaction. An end-capping monomer in the present context is a monomer with only one reactive site which is capable of end-capping a growing polymer chain in a polymerization reaction.

Essentially individual monomers and also mixtures of monomers may be produced by the methods of the present invention. In one embodiment monomer mixtures comprising a polymerizable bis(phthalimide) monomer and an end-capping bis(phthalimide) monomer may be produced by selection of the appropriate combination of reactants. For example, a portion of the anhydride reactant may be an anhydride of formula (IV) wherein Z is selected so as to be non-reactive in subsequent polymerization reactions, e.g., wherein p is 0 (i.e. formula (IV) is phthalic anhydride). The remaining portion of anhydride reactant may be an anhydride of formula (IV) wherein Z is selected so as to be reactive in subsequent polymerization reactions, e.g., wherein p is 1 and Z is chlorine (i.e. formula (IV) is a chlorophthalic anhydride). The reaction of a mixture of the two specified anhydrides with a diamine reactant can provide a mixture comprising both polymerizable monomer (formula (II) in which m and n are each 1, $R^2$ and $R^3$ are each chlorine, and q is 1) and end-capping monomer (formula (II) in which m is 0, n is 1, and $R^3$ is chlorine, and q is 1), suitable for use in a subsequent polymerization reaction.

Alternatively, the melt synthesis reactants may include a mono-amine reactant, such as aniline, which will also produce an end-capping monomer through reaction with a reactive anhydride, that is an anhydride bearing a group reactive in a subsequent polymerization reaction. In suitable embodiments aniline or other mono-amine may be reacted alone with reactive anhydride to produce essentially an end-capping monomer by itself, or aniline (or other mono-amine) in combination with a diamine may be reacted with reactive anhydride to produce a mixture containing an end-capping monomer and a polymerizable monomer. Similarly, a triamine, such as triaminopyrimidine, may be reacted alone with reactive anhydride to produce essentially a branching monomer by itself, or triaminopyrimidine (or other triamine) in combination with a diamine and a monoamine may be reacted with reactive anhydride to produce a mixture containing a branching monomer, an end-capping monomer and a polymerizable monomer. The various permutations for combining mono-, di-, and tri-amines to provide essentially individual phthalimides or mixtures of phthalimides will be obvious to those with skill in the art.

In a preferred embodiment, the methods described herein are suitable for the synthesis of bis(chlorophthalimide) of formula (I), and isomers thereof, such as in formulas (V) and (VI), and the para (with respect to the central phenyl ring) isomers of formulas (I), (V) and (VI):

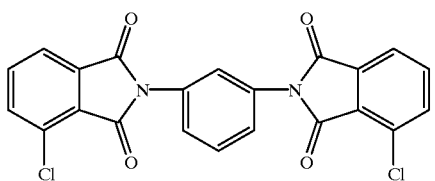

(V)

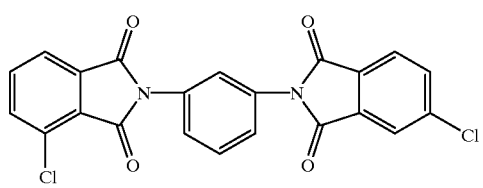

(VI)

The method may also be employed in the production of mixtures of isomeric bis(chlorophthalimide)s (I), (V), and (VI) from a mixture of meta-phenylenediamine, 3-chlorophthalic anhydride, and 4-chlorophthalic anhydride, as detailed in Example 3.

One embodiment of the present invention provides a method for the solventless synthesis of phthalimides of formula (II) which comprises heating a mixture of at least one amine reactant and at least one anhydride reactant in a solventless environment to a first temperature sufficient to allow the reactants to at least partially condense, while minimizing loss through sublimation; and subsequently increasing the temperature by an amount sufficient to melt the reaction mixture, thereby completing formation of the reaction product. The reaction may optionally be conducted completely or partially under reduced pressure.

The first temperature is sufficient to allow the starting materials to at least partially condense. At least partially condense in the present context means that the initial reaction between amine and anhydride to form amic acid is at least partially complete with no or at least minimal loss of any reactant volatile under the reaction conditions. Preferably the initial reaction is greater than about 50%, more preferably greater than about 80%, and most preferably greater than about 90% complete. Depending upon factors such as the reactants used, the choice of first temperature, and the time of reaction at said first temperature, none or a fraction of the at least partially condensed reaction product may further react to form phthalimide or phthalimide mixture. Also, depending upon such factors as the immediately preceding three parameters, the reaction mixture may partially melt, or it may remain substantially solid, or it may partially or completely melt and then form substantially a solid as the initial condensation reaction proceeds at said first temperature. A low first temperature is preferred in order to minimize loss of material through sublimation. For example, for the reaction between meta-phenylenediamine and 4-chlorophthalic anhydride, the first temperature is in the range of from about 60 ° C. to about 120° C. and is preferably about 100° C. For other reactants, the initial low temperature is readily selected empirically, according to the choice of reactants and product, and vacuum level. Water evolution and HPLC analyses indicate that considerable imidization may occur during the initial condensation reaction, and higher melting solids may be formed.

The rate of heating the reaction mixture to achieve said first temperature is controlled so as to minimize loss of any reactant through sublimation. Said heating rate is readily selected empirically, according to the choice of reactants and product, and vacuum level.

The reaction temperature is then increased to a second, higher temperature sufficient to melt the reaction mixture, thereby essentially completing formation of the product phthalimide or phthalimide mixture of formula (II). The rate of heating the reaction mixture to achieve said second temperature is also controlled so as to minimize loss of any reactant through sublimation. Said heating rate is readily selected empirically, according to the choice of reactants and product, and vacuum level.

In a preferred embodiment the second reaction temperature approaches the melting point of the desired phthalimide product (for example, 336–339° C. for the bis(chlorophthalimide)s of formula (I)). The entire reaction may be performed partially or wholly under reduced pressure to ensure completion, as detailed in Example 1, The reaction product obtained is substantially free from amic acid impurities such as those shown in formulas (VII) and (VIII):

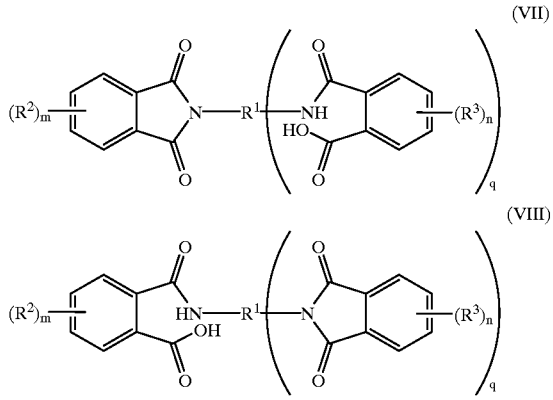

(VII)

(VIII)

wherein $R^1$, $R^2$, $R^3$, m, n, and q are as defined previously. The reaction product is also typically much more free flowing and of a higher bulk density than product derived from a catalyzed reaction in solution.

In a second embodiment, a method for the solventless synthesis of phthalimides of formula (II) is provided comprising heating a mixture of at least one amine reactant and at least one anhydride reactant in a solventless environment to a first temperature sufficient to allow the reactants to at least partially condense, while minimizing loss through sublimation as described above; cooling the resultant mixture; and subsequently heating the reaction mixture to a second temperature at which it remains substantially solid under reduced pressure, thereby essentially completing formation of the reaction product.

The first temperature is sufficient to allow the starting materials to at least partially condense. A low temperature is preferred in order to minimize loss of material through sublimation. The rate of heating the reaction mixture to achieve said first temperature is also controlled so as to minimize loss of any reactant through sublimation. Said heating rate is readily selected empirically, according to the choice of reactants and product, and vacuum level.

Following cooling, the substantially solid reaction mixture is transferred to a vacuum oven and heated again at a second temperature under reduced pressure, thereby essentially completing formation of product phthalimide or phthalimide mixture. The second temperature is selected so that the product formation is essentially completed while the reaction mixture remains substantially in the solid state. The rate of heating the reaction mixture to achieve said second temperature is also controlled so as to minimize loss of any reactant through sublimation. Said heating rate is readily selected empirically, according to the choice of reactants and product, and vacuum level.

Example 2 provides an example of the melt-solid state synthesis of bis(chlorophthalimide) (I), wherein the first low temperature is about 130° C. and the second temperature is about 150° C. under a vacuum of 25 millimeters of mercury (mm Hg).

An especially advantageous feature of this embodiment is that essentially complete conversion to product can be achieved at much lower temperatures by conducting the reaction under reduced pressure. However, under these conditions the initial amine condensation must be completed to the furthest extent possible during the first low temperature melt. If not, material is likely to be lost to sublimation since no mixing will occur during a subsequent higher temperature solid state reaction.

The foregoing drawback may be remedied by a third embodiment of the present invention, wherein an amic acid or amic acid mixture, produced, for example, by solvent reaction of at least one amine reactant and at least one anhydride reactant, is used as the starting material for solid state synthesis of phthalimides of formula (II).

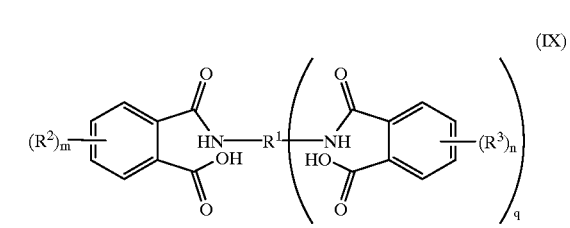

(IX)

Amic acids suitable for use in the present invention include those represented by formula (IX) wherein $R^1$, $R^2$, $R^3$, m, n, and q are as defined previously. Although essentially homogeneous amic acids or amic acid mixtures are contemplated for use in the present embodiment, those skilled in the art will recognize that amic acids suitable for use include those containing minor amounts of the corresponding phthalimides or mixed amic acid-phthalimides (i.e. compounds with both amic acid and phthalimide moieties in the same molecule) resulting from at least partial imidization, since some phthalimide formation may occur in the course of the initial reaction between the at least one amine reactant and the at least one anhydride reactant.

Heating an amic acid or amic acid mixture in a solventless environment to a temperature at which it remains substantially in a solid state under reduced pressure provides the product phthalimide or mixture of phthalimides. The rate of heating the reaction mixture is also controlled so as to minimize loss of any reactant through sublimation. Said heating rate is readily selected empirically, according to the choice of reactants and product, and vacuum level.

Solid products obtained by the solid state reaction of amic acids are again typically more free-flowing and of higher bulk density than those obtained by conventional solution reactions. While solid-state synthesis may require a solvent-based reaction to produce the amic acid or amic acid mixture, the concentrations of amic acids in solution may be much higher than the concentrations of the corresponding phthalimides in slurries typically obtained with solvent reactions. Solid state synthesis from amic acids is detailed in Example 4, wherein isomeric bis(chlorophthalimide)s (I), (V), and (VI) are synthesized from the bis(amic acid) formed by reaction of meta-phenylenediamine with 3-chlorophthalic anhydride and 4-chlorophthalic anhydride. Example 5 illustrates synthesis of bis(chlorophthalimide) (II) from the bis(amic acid) of meta-phenylenediamine and 4-chlorophthalic anhydride.

The total reaction time required for solventless synthesis in any embodiment of the present invention is often significantly reduced compared to conventional reaction times, for example in a solvent. The present invention is capable of achieving a total reaction time that does not exceed three hours, which is typically one-half the time required for a catalyzed reaction conducted in a solvent such as anisole, in which impurities such as those in formulas (VII) and (VII) may still be present.

The phthalimide-containing products produced by the method and method variations of the present invention may be further purified by any convenient method known in the art. Illustrative, non-limiting examples of purification methods may include a sublimation and/or a zone refining step. Because of the solventless nature of the reaction, the step of stripping the solvent is avoided. Sublimation purification is particularly suitable for use with bis(phthalimide) products contaminated with impurities such as a mono-imide adduct of meta-phenylenediamine. Example 6 details the sublimation purification of yellow bis(chlorophthalimide) contaminated with 0.1% mono-imide adduct of meta-phenylenediamine.

In any of the embodiments of the present invention a catalyst may optionally be present. Representative catalysts include, but are not limited to, sodium phenyl phosphinate and tertiary amines. Preferably, the methods of the present invention are conducted in the absence of a catalyst.

The present methods provide for the preparation of a wide variety of products, including polymerizable monomers, end-capped monomers, branching monomers, and mixtures thereof. Variable reaction melt temperatures can be achieved through selection of reactant structure, reactant concentration, and through use of multiple amines or anhydrides, such as a 3-chlorophthalic anhydride and 4-chlorophthalic anhydride isomer mix. Selection of reactant structure, reactant concentration, and use of multiple amines or anhydrides also permits the synthesis of phthalimides or mixtures of phthalimides which possess controlled, differential monomer reactivity. For example, through selection of anhydrides with differently reactive groups, phthalimide monomers and mixtures of monomers can be prepared which have controlled, differential monomer reactivity under different polymerization reaction conditions.

The following examples are provided to illustrate exemplary embodiments in accordance with the method and method variations of the present invention. It should be understood that the examples are given for the purpose of illustration and do not limit the invention.

EXAMPLE 1

Synthesis of Bis(chlorophthalimide) (I)

Into a glass reactor tube was charged 41.7512 grams (g) (228.7 mmol) 4-chlorophthalic anhydride and 12.3907 g (114.6 mmol) meta-phenylenediamine. The tube was placed in a reactor and evacuated to less than 1 millibar (mbar) and refilled with nitrogen. This purging process was repeated 3 times. The stirred mixture was then heated to a temperature of about 100° C. at about 1 bar for about 20 minutes. After about 10 minutes, it was observed that large amounts of moisture began to appear in the upper, cooler areas of the reaction tube. The reactor temperature was slowly increased in 25° C. increments at about 5° C. per minute until a reaction temperature of about 380° C. was obtained. During the course of the temperature increase, the pressure of the system was also gradually reduced to a final pressure of 0.6 mbar. After holding at 380° C. for 5 minutes, the tube was cooled and a sample of the bulk product was taken. The central core of the reactor contained fine crystals that had recrystallized from the melt. These crystals were also sampled. It is hypothesized that these crystals had cooled more slowly due to the insulating layer of solidified product surrounding the reactor core. The solidified bulk product and crystal samples were submitted for high-pressure liquid chromatography (HPLC) analysis and microscopy. The bulk product was approximately 98.6% pure, while the crystal samples were analytically pure.

EXAMPLE 2

Synthesis of Bis(chlorophthalimide) (I)

To a 100 milliliter (ml) round bottomed flask equipped with a magnetic stir bar and nitrogen inlet was added 2.0 g (0.01849 mol) meta-phenylenediamine and 6.753 g (0.036989 mol) 4-chlorophthalic anhydride. The mixture was heated in a bath at 130° C. for 3 hours. The resultant solid was then cooled to room temperature and a sample removed for HPLC analysis. The sample consisted of a mixture of product, amic acids and mono-imide adduct of meta-phenylenediamine. The solid was transferred to a vacuum oven and heated overnight at 150° C. under a vacuum of 25 mm. HPLC analysis of the heated solid showed that the amic acids were converted to bis (chlorophthalimide) (I), with the major impurity being residual mono-imide adduct.

EXAMPLE 3

Synthesis of Isomeric Bis(chlorophthalimide)s (I), (V), and (VI)

To a flat bottomed cylindrical melt reactor equipped with an overhead mechanical glass corkscrew stirrer, and nitrogen and vacuum inlets through a three-way stop cock, was added 7.3024 g (0.04 mol) 3-chlorophthalic anhydride, 7.3024 g (0.04 mol) 4-chlorophthalic anhydride and 4.3256 g (0.04 mol) meta-phenylenediamine. The solids were mixed by stirring and the reactor was heated in a 170° C. bath for 1 hr. It was observed that the mixture melted but quickly resolidified and stopped the stirrer. The bath temperature was raised to 290° C., with some melting and stirring, and held for 1 hour. Solids were removed from the stirrer and returned to the bulk material, and the temperature was raised to 320° C. with stirring for one hour. Vacuum was occasionally applied during the heating, but the pressure in the reactor was not measured, and little vacuum appeared to be achieved. HPLC analysis of the solid bulk product showed clean conversion to the three isomeric bis (chlorophthalimide)s (I), (V), and (VI).

EXAMPLE 4

Solid-State Synthesis of Isomeric Bis (chlorophthalimide)s (I), (V), and (VI) From Bis (Amic Acid)s Bis(amic acid)s of meta-phenylenediamine were prepared from 3-chlorophthalic anhydride and 4-chlorophthalic anhydride as follows. To a 500 ml round bottomed flask equipped with a magnetic stir bar and nitrogen inlet was added 7.3024 g (0.04 mol) 3-chloro-phthalic anhydride, 7.3024 g (0.04 mol) 4-chlorophthalic anhydride and 100 ml tetrahydrofuran (THF). The mixture was stirred to make a solution, and 4.3256 g (0.04 m) meta-phenylenediamine was added. The reaction mixture was stirred at room temperature for 2 hours, and concentrated on a rotary evaporator. Methylene chloride was added, causing precipitation of an oily solid. Solvent was removed on the rotary evaporator and vacuum line. HPLC analysis confirmed the preparation of the solid bis (amic acid)s.

About 200 mg of the prepared solid bis(amic acid)s were placed in a glass vial and heated in a 150 ° C. vacuum oven overnight. HPLC analysis confirmed the imidization of the bis(amic acid)s to the three isomeric bis (chlorophthalimide)s of formulas (I), (V), and (VI).

EXAMPLE 5

Solid-State Synthesis of Bis(chlorophthalimide) (I) From the Bis(Amic Acid) of meta-Phenylenediamine and 4-Chlorophthalic Anhydride To a 500 ml three-necked round bottomed flask equipped with an addition funnel, mechanical stirrer, thermometer, and nitrogen inlet was added 5.407 g (0.05 mol) meta-phenylenediamine and 25 ml o-dichlorobenzene. The resultant slurry was stirred at room temperature while a solution of 18.256 g (0.1 mol) 4-chlorophthalic anhydride in 60 ml o-dichlorobenzene was added dropwise. No significant exotherm was observed, and a slurry formed. Stirring was continued for 2 hours, and the reaction was sampled. HPLC analysis of the sample indicated a mixture of amic acids and residual anhydride with only a trace of diamine. The solids were filtered to remove the mono(amic acid)s and phthalic anhydride and some of the bis(amic acid)s.

About 200 mg of the solid amic acids were placed in a glass vial and heated in a vacuum oven at 150 ° C. for about 3 hours. HPLC analysis confirmed essentially complete imidization of the amic acids to yield a mixture of bis (chlorophthalimide) with the mono-imide adduct of meta-phenylenediamine as an impurity.

EXAMPLE 6

Sublimation of Bis(chlorophthalimide) (I)

3.078 g of yellow bis(chlorophthalimide) contaminated with 0.1% mono-imide adduct of meta-phenylenediamine were added to a water-cooled sublimator equipped with a vacuum hose inlet. The sublimator was placed in a 270° C. bath, and the temperature was raised to 352° C. over a 95 minute period. White crystals were observed on the cold finger and sides of the sublimator, leaving a dark yellow residue behind. Analysis of the sublimed, white crystals showed no detectable mono-imide adducts.

The present methods provide an improved, environmentally sound, economical process for producing phthalimides, such as bis(chlorophthalimide)s, suitable for use as intermediates in the production of polyetherimides. The method and method variations of the present invention provide good reaction rates and high percent conversion to a product isolable in a convenient, usable physical form. By eliminating or at least minimizing losses of volatile reactants under the process conditions the reactants are kept at the proper stoichiometric ratio for optimum conversion efficiency. By eliminating solvents in the reaction process, the necessity for overhead condensers and decanters is eliminated. The elimination of wet solvent also reduces the hydraulic load on the solvent drying column, possibly reducing its size requirement. There is also the elimination of various solvent emission points around flanges and pump fields. Finally, there may be an added cost benefit when a catalyst is not employed. In addition the absence of a catalyst may result in a product without catalyst residues therein.

While the present invention has been described with reference to particular embodiments thereof, it will be understood that numerous modifications may be made by those skilled in the art without actually departing from the spirit and scope of the invention as defined in the appended claims.

What is claimed is:

1. A method for the synthesis of a phthalimide or phthalimide mixture from an amic acid or amic acid mixture derived from reaction of at least one amine reactant and at least one anhydride reactant, comprising:

heating the amic acid or amic acid mixture to a temperature at which it remains substantially solid in a solventless environment under reduced pressure, thereby essentially completing formation of a phthalimide or phthalimide mixture having the structure (II)

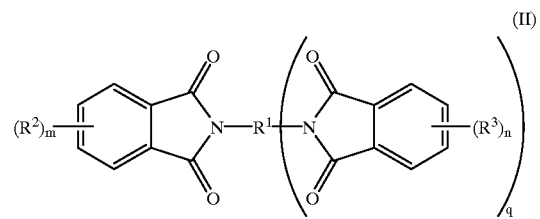

wherein $R^1$ is a mono-, di-, or trivalent organic radical; $R^2$ and $R^3$ are each independently halogen, nitro, nitroso, alkyl, aryl; m and n each independently have values between 0 and 4 inclusive; and q is 0, 1, or 2.

2. The method of claim 1, further comprising purifying the phthalimide-containing product by sublimation.

3. The method of claim 1, wherein the amine is at least one member selected from the group consisting of meta-phenylenediamine, para-phenylenediamine, and aniline.

4. The method of claim 1, wherein the anhydride is at least one member selected from the group consisting of 3-chlorophthalic anhydride, 4-chlorophthalic anhydride, phthalic anhydride, and dichlorophthalic anhydride.

5. The method of claim 1, wherein a mixture of isomeric bis(chlorophthalimide)s is formed from 3-chloro-phthalic anhydride and 4-chlorophthalic anhydride.

6. The method of claim 1, wherein the reactants are selected to produce a reaction product that is a polymerizable monomer, essentially an end-capping monomer, a branching monomer.

7. A method for the catalyst-free synthesis of a phthalimide or phthalimide mixture, comprising:

heating a mixture of at least one amine reactant and at least one anhydride reactant in a catalyst-free, solventless environment to a first temperature sufficient to allow the reactants to at least partially condense; then heating the solid reaction mixture in a catalyst-free, solventless environment at a second temperature sufficient to melt the reaction mixture, thereby essentially completing formation of a phthalimide or phthalimide mixture having the structure (II)

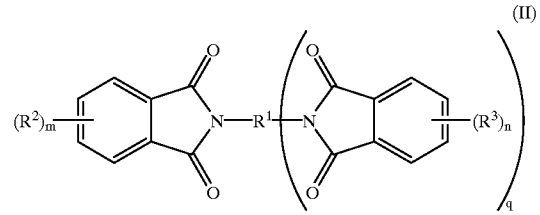

wherein $R^1$ is a mono-, di-, or trivalent organic radical; $R^2$ and $R^3$ are each independently halogen, nitro, nitroso, alkyl, aryl; m and n each independently have values between 0 and 4 inclusive; and q is 0, 1, or 2.

8. The method of claim 7, wherein the second temperature approaches the melting point of the phthalimide or phthalimide mixture.

9. The method of claim 7, wherein the heating is conducted completely or partially under reduced pressure.

10. The method of claim 7, further comprising purifying the phthalimide-containing product by sublimation.

11. The method of claim 7 wherein the amine is at least one member selected from the group consisting of meta-phenylenediamine, para-phenylenediamine, and aniline.

12. The method of claim 7 wherein the anhydride is at least one member selected from the group consisting of 3-chlorophthalic anhydride, 4-chlorophthalic anhydride, phthalic anhydride, and dichlorophthalic anhydride.

13. The method of claim 7 wherein a mixture of isomeric bis(chlorophthalimide)s is formed from 3-chlorophthalic anhydride and 4-chlorophthalic anhydride.

14. The method of claim 7 wherein the reactants are selected to produce a reaction product that is essentially a polymerizable monomer, essentially an end-capping monomer, a branching monomer, or a combination thereof.

15. A method for the catalyst-free synthesis of a phthalimide or phthalimide mixture, comprising:

heating a mixture of at least one amine reactant and at least one anhydride reactant in a catalyst-free, solventless environment to a first temperature sufficient to allow the reactants to at least partially condense; then cooling the reaction mixture; and heating the reaction mixture in a catalyst-free, solventless environment to a second temperature at which it remains substantially solid under reduced pressure, thereby essentially completing formation of a phthalimide or phthalimide mixture having the structure (II)

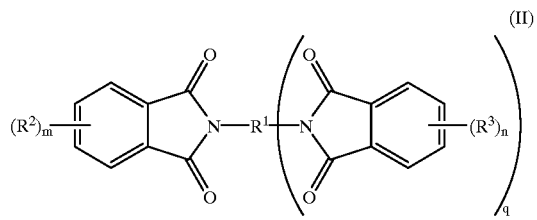

wherein $R^1$ is a mono-, di-, or trivalent organic radical; $R^2$ and $R^3$ are each independently halogen, nitro, nitroso, alkyl, aryl; m and n each independently have values between 0 and 4 inclusive; and q is 0, 1, or 2.

16. The method of claim 15, further comprising purifying the phthalimide-containing product by sublimation.

17. The method of claim 15, wherein the amine is at least one member selected from the group consisting of meta-phenylenediamine, para-phenylenediamine, and aniline.

18. The method of claim 15, wherein the anhydride is at least one member selected from the group consisting of 3-chlorophthalic anhydride, 4-chlorophthalic anhydride, phthalic anhydride, and dichlorophthalic anhydride.

19. The method of claim 15, wherein a mixture of isomeric bis(chlorophthalimide)s is formed from 3-chlorophthalic anhydride and 4-chlorophthalic anhydride.

20. The method of claim 15, wherein the reactants are selected to produce a reaction product that is a polymerizable monomer, essentially an end-capping monomer, a branching monomer, or a combination thereof.

21. A method for the catalyst-free synthesis of a phthalimide or phthalimide mixture from an amic acid or amic acid mixture derived from reaction of at least one amine reactant and at least one anhydride reactant, comprising:

heating the amic acid or amic acid mixture to a temperature at which it remains substantially solid in a catalyst-free solventless environment under reduced pressure, thereby essentially completing formation of a phthalimide or phthalimide mixture having the structure (II)

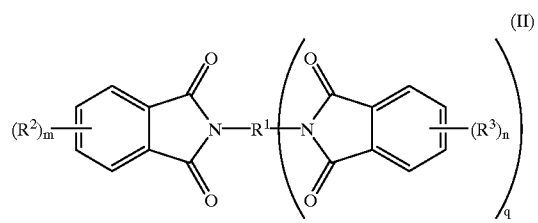

wherein $R^1$ is a mono-, di-, or trivalent organic radical; $R^2$ and $R^3$ are each independently halogen, nitro, nitroso, alkyl, aryl; m and n each independently have values between 0 and 4 inclusive; and q is 0, 1, or 2.

22. The method of claim 21, further comprising purifying the phthalimide-containing product by sublimation.

23. The method of claim 21, wherein the amine is at least one member selected from the group consisting of meta-phenylenediamine, para-phenylenediamine, and aniline.

24. The method of claim 21, wherein the anhydride is at least one member selected from the group consisting of 3-chlorophthalic anhydride, 4-chlorophthalic anhydride, phthalic anhydride, and dichlorophthalic anhydride.

25. The method of claim 21, wherein a mixture of isomeric bis(chlorophthalimide)s is formed from 3-chlorophthalic anhydride and 4-chlorophthalic anhydride.

26. The method of claim 21, wherein the reactants are selected to produce a reaction product that is essentially a polymerizable monomer, essentially an end-capping monomer, a branching monomer, or a combination thereof.

27. A method for the synthesis of a phthalimide or phthalimide mixture from an amic acid or amic acid mixture derived from reaction of at least one amine reactant selected from the group consisting of meta-phenylenediamine and para-phenylenediamine, and at least one anhydride reactant selected from the group consisting of 3-chlorophthalic anhydride and 4-chlorophthalic anhydride, comprising:

heating the amic acid or amic acid mixture to a temperature at which it remains substantially solid in a solventless environment under reduced pressure, thereby essentially completing formation of a phthalimide or phthalimide mixture having the structure (II)

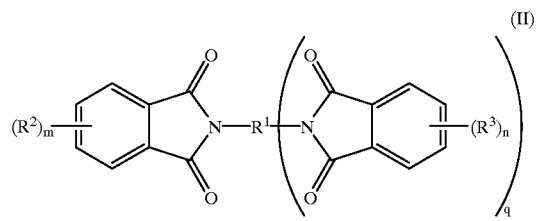

wherein $R^1$ is a phenylene radical; $R^2$ and $R^3$ are each independently chloro; m and n are each 1; and q is 1.

28. A method for the catalyst-free synthesis of a phthalimide or phthalimide mixture, comprising:

heating a mixture of at least one amine reactant selected from the group consisting of meta-phenylenediamine and para-phenylenediamine, and at least one anhydride reactant selected from the group consisting of 3-chlorophthalic anhydride and 4-chlorophthalic anhydride in a catalyst-free, solventless environment to a first temperature sufficient to allow the reactants to at least partially condense; then heating the solid reaction mixture in a catalyst-free, solventless environment at a second temperature sufficient to melt the reaction mixture, thereby essentially completing formation of a phthalimide or phthalimide mixture having the structure (II)

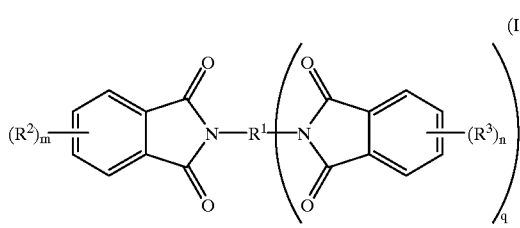
(II)

wherein R¹ is a phenylene radical; R² and R³ are each independently chloro; m and n are each 1; and q is 1.

29. A method for the catalyst-free synthesis of a phthalimide or phthalimide mixture, comprising:

heating a mixture of at least one amine reactant selected from the group consisting of meta-phenylenediamine and para-phenylenediamine and at least one anhydride reactant selected from the group consisting of 3-chlorophthalic anhydride and 4-chlorophthalic anhydride in a catalyst-free, solventless environment to a first temperature sufficient to allow the reactants to at least partially condense; then cooling the reaction mixture; and heating the reaction mixture in a catalyst-free, solventless environment to a second temperature at which it remains substantially solid under reduced pressure, thereby essentially completing formation of a phthalimide or phthalimide mixture having the structure (II)

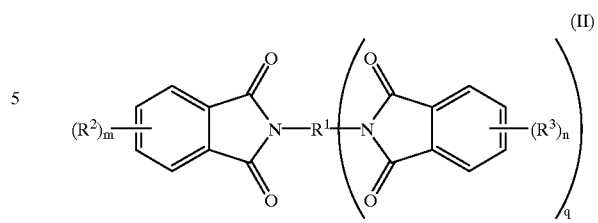
(II)

wherein R¹ is a phenylene radical; R² and R³ are each independently chloro; m and n are each 1; and q is 1.

30. A method for the catalyst-free synthesis of a phthalimide or phthalimide mixture from an amic acid or amic acid mixture derived from reaction of at least one amine reactant selected from the group consisting of meta-phenylenediamine and para-phenylenediamine and at least one anhydride reactant selected from the group consisting of 3-chlorophthalic anhydride and 4-chlorophthalic anhydride, comprising:

heating the amic acid or amic acid mixture to a temperature at which it remains substantially solid in a catalyst-free solventless environment under reduced pressure, thereby essentially completing formation of a phthalimide or phthalimide mixture having the structure (II)

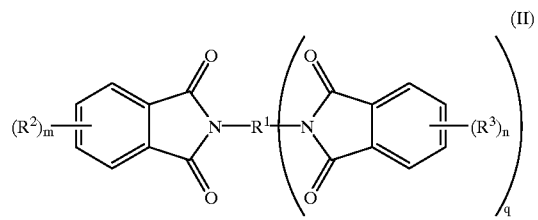
(II)

wherein R¹ is a phenylene radical; R² and R³ are each independently chloro; m and n are each 1; and q is 1.

* * * * *